United States Patent
Takayama et al.

(10) Patent No.: US 12,331,092 B2
(45) Date of Patent: Jun. 17, 2025

(54) LEUCINE-RICH ALPHA2 GLYCOPROTEIN COMPOSITION

(71) Applicants: SEKISUI MEDICAL CO., LTD., Tokyo (JP); NATIONAL INSTITUTES OF BIOMEDICAL INNOVATION, HEALTH AND NUTRITION, Ibaraki (JP)

(72) Inventors: Shigeo Takayama, Tokyo (JP); Tetsuji Naka, Ibaraki (JP); Satoshi Serada, Ibaraki (JP)

(73) Assignees: SEKISUI MEDICAL CO., LTD., Tokyo (JP); NATIONAL INSTITUTES OF BIOMEDICAL INNOVATION, HEALTH AND NUTRITION, Ibaraki (JP)

( * ) Notice: Subject to any disclaimer, the term of this patent is extended or adjusted under 35 U.S.C. 154(b) by 1079 days.

(21) Appl. No.: 17/282,325

(22) PCT Filed: Oct. 8, 2019

(86) PCT No.: PCT/JP2019/039565
§ 371 (c)(1),
(2) Date: Apr. 1, 2021

(87) PCT Pub. No.: WO2020/075692
PCT Pub. Date: Apr. 16, 2020

(65) Prior Publication Data
US 2022/0127314 A1 Apr. 28, 2022

(30) Foreign Application Priority Data
Oct. 9, 2018 (JP) .................................. 2018-190904

(51) Int. Cl.
*C07K 14/47* (2006.01)
*G01N 33/68* (2006.01)

(52) U.S. Cl.
CPC ....... *C07K 14/473* (2013.01); *G01N 33/6803* (2013.01)

(58) Field of Classification Search
CPC ...... C07K 14/473; G01N 33/52; G01N 33/68; G01N 33/6803; G01N 2400/00
See application file for complete search history.

(56) References Cited

U.S. PATENT DOCUMENTS

2013/0052655 A1 2/2013 Kobayashi et al.

FOREIGN PATENT DOCUMENTS

| JP | 2010-286279 A | | 12/2010 |
| JP | 2011116697 A | * | 6/2011 |
| JP | 2012-92095 A | | 5/2012 |
| JP | 2016-79170 A | | 5/2016 |
| WO | WO 2011/125877 A1 | | 10/2011 |

OTHER PUBLICATIONS

Dodia et al., J Ind Microbiol Biotechnol, 2008, 35:121-131.*
Chinese Office Action for Chinese Application No. 201980065023. 1, dated Jul. 31, 2024, with English translation.
Singaporean Written Opinon for Singaporean Application No. 11202103373Q, dated Aug. 21, 2024.
Japanese Office Action for Japanese Application No. 2020-551154, dated Jul. 19, 2023, with an English translation.
International Serch Report issued in PCT/JP2019/039565 (PCT/ISA/210), dated Nov. 12, 2019.
O'Donnell et al., "Molecular characterization and expression analysis of leucine-rich α2-glycoprotein, a novel marker of granulocytic differentiation", Journal of Leukocyte Biology, vol. 72, Sep. 2002, 8 pages.
Serada et al., "ITRAQ-based proteomic identification of leucine-rich α-2 glycoprotein as a novel inflammatory biomarker in autoimmune diseases", Ann Rheum Dis 2010, Oct. 22, 2009, pp. 770-774, 7 pages.
Written Opinion of the International Searching Authority issued in PCT/JP2019/039565 (PCT/ISA/237), dated Nov. 12, 2019.
Athens Research and Technology, Inc., SDS—Safety Data Sheet, Leucine-rich Alpha 2 Glycoprotein 1, Human Plasma (LRG1) Product No. 16-16-121807, Nov. 14, 2013.
Codina et al., "Cytochrome c-induced lymphocyte death from the outside in: inhibition by serum leucine-rich alpha-2-glycoprotein-1," Apoptosis (2010), vol. 15, pp. 139-152; published online Oct. 23, 2009.
Exended European Search Report issued Jun. 13, 2022, in European Patent Application No. 19871764.7.
IBL—Instructions for Use Code No. 27785, Mouse LRG Assay Kit—IBL, Jul. 2015.
Chinese Office Action and Search Report for Chinese Application No. 201980065023.1, dated Nov. 22, 2023, with English translation.
"Leucine-rich Alpha 2 Glycoprotein 1, Human Plasma (LRG1)," Athens Research and Technology, Inc., Nov. 14, 2013, pp. 2-3 (6 pages total).
"Mouse LRG Assay Kit—IBL," IBL, Jul. 31, 2015, pp. 1-2.
Codina et al., "Cytochrome c-induced lymphocyte death from the outside in: inhibition by serum leucine-rich alpha-2-glycoprotein-1," Apoptosis, Oct. 23, 2009, vol. 15 pp. 139-152.
Singaporean Search Report and Written Opinion for corresponding Singaporean Application No. 11202103373Q, dated Nov. 18, 2022.
European Office Action for European Application No. 19 871 764.7, dated Apr. 4, 2023.
English translation of International Preliminary Report on Patentability and Written Opinion mailed Apr. 22, 2021, in PCT/JP2019/039565.
European Office Action dated Oct. 30, 2023 for Application No. 19 871 764.7.
Korean Office Action for Korean Application No. 10-2021-7013499, dated Nov. 21, 2024, with English translation.

* cited by examiner

*Primary Examiner* — Hong Sang
(74) *Attorney, Agent, or Firm* — Birch, Stewart, Kolasch & Birch, LLP

(57) ABSTRACT

An object is to provide a leucine-rich α2 glycoprotein composition comprising leucine-rich α2 glycoprotein and having excellent preservation stability. The object can be achieved by a leucine-rich α2 glycoprotein composition comprising leucine-rich α2 glycoprotein and having a pH of 7.0 to 9.3.

10 Claims, 2 Drawing Sheets

[FIG. 1]
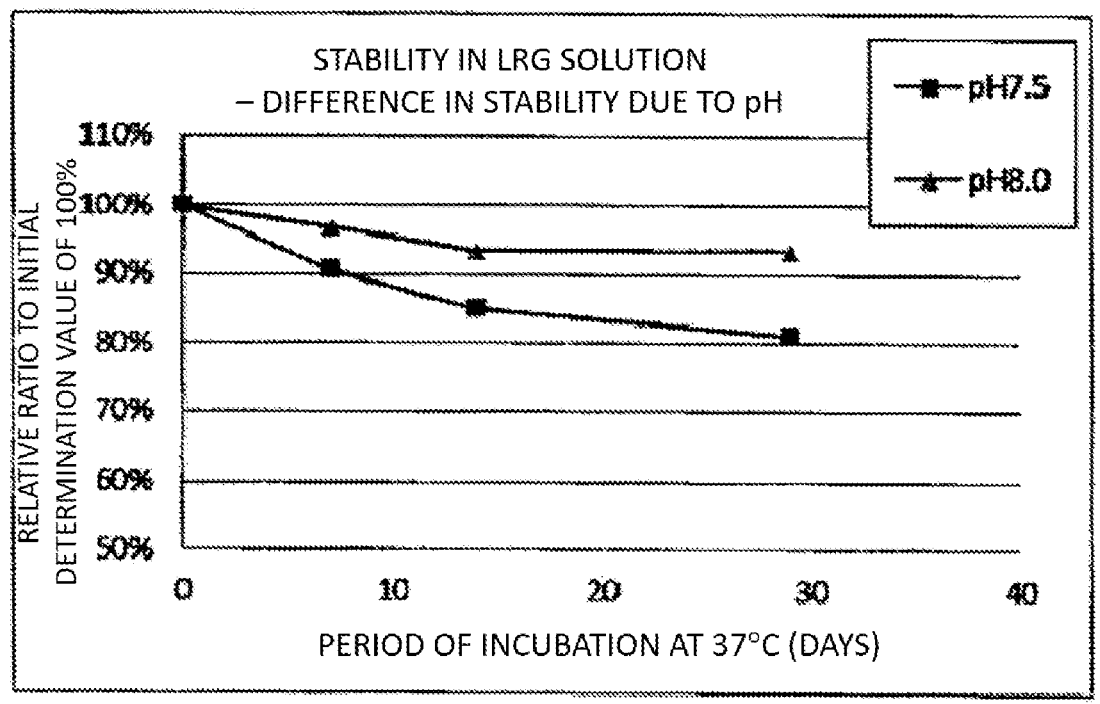
[FIG. 2]
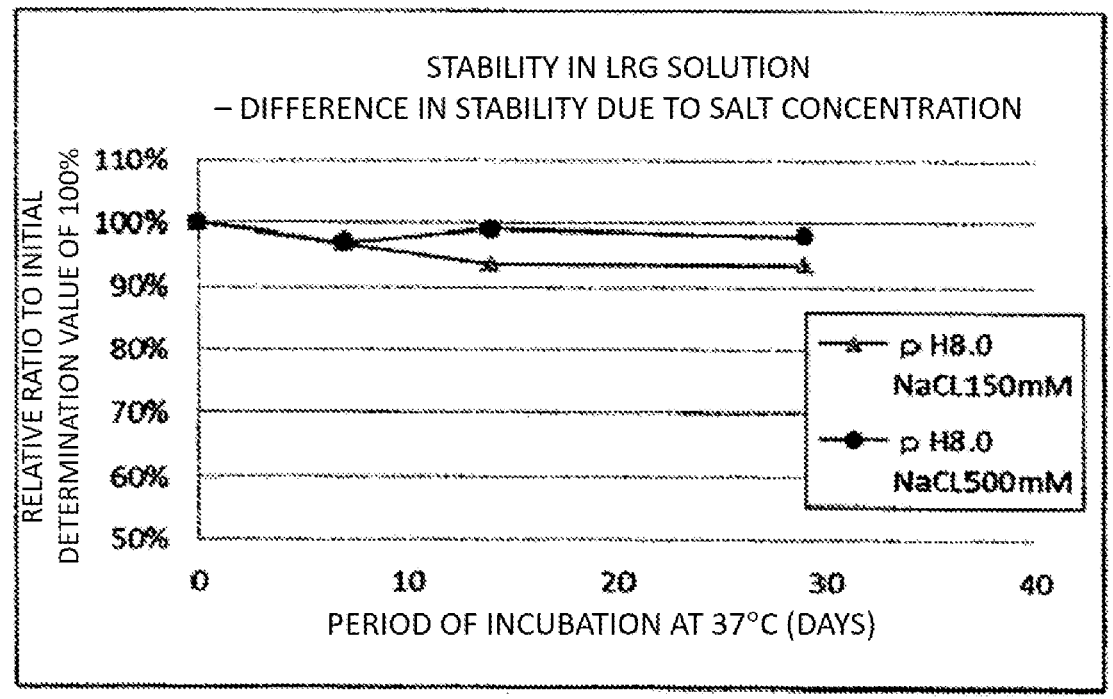

[FIG. 3]
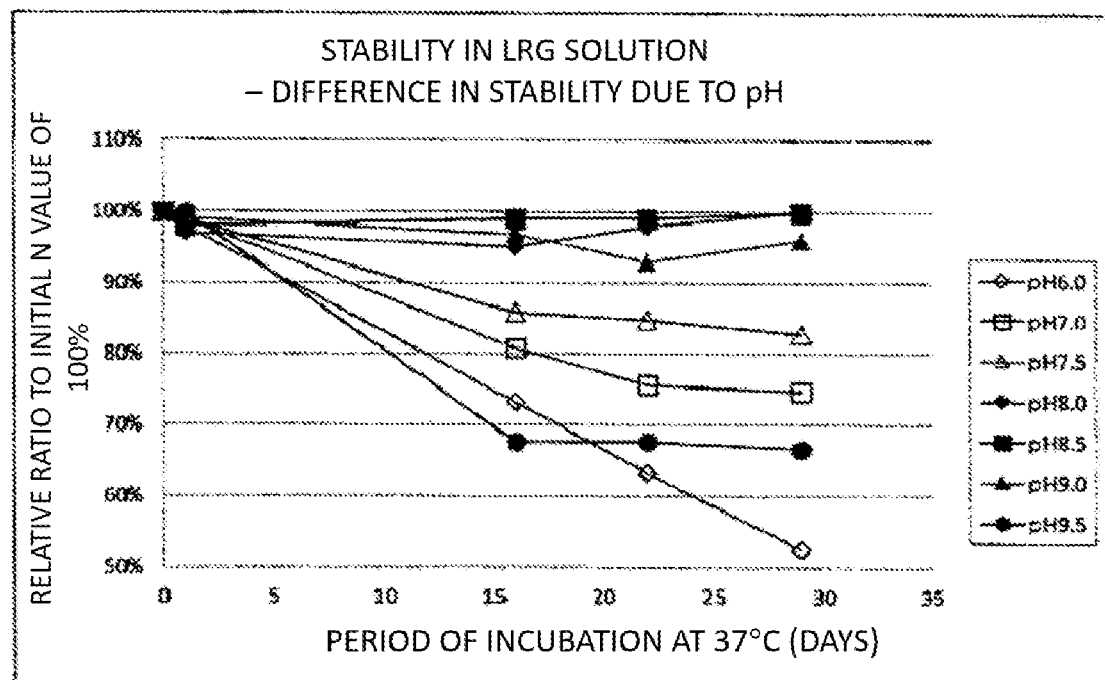

LEUCINE-RICH ALPHA2 GLYCOPROTEIN COMPOSITION

TECHNICAL FIELD

The present invention relates to a leucine-rich α2 glycoprotein composition. More specifically, the invention relates to a composition with which leucine-rich α2 glycoprotein can be preserved stably for a long time.

BACKGROUND ART

Leucine-rich α2 glycoprotein (hereinafter, sometimes referred to as LRG) is one of serum proteins. It is reported that LRG is a glycoprotein of about 50 kDa and is secreted from neutrophils (Non-Patent Document 1).

Recently, the relevance of LRG in a biological sample to specific diseases has been studied. For example, Patent Document 1 reports that detecting LRG in a biological sample is useful for testing autoimmune diseases such as Behcet's disease.

To quantitatively determine the component to be measured in a biological sample, it is necessary to use a calibration sample. The calibration sample is a sample containing the component to be measured and is used as an internal standard, a concentration calibration standard (calibrator) or the like. To obtain an accurate quantitative value, a calibration sample which is stable in spite of the passage of time or the temperature is required. That is, it is believed that, when the component to be measured in the calibration sample is decomposed and/or denatured during the preservation, the measured value is also affected. For quantitative determination of LRG, a method using the enzyme-linked immunosorbent assay (ELISA) or the like has been known so far, but the calibration sample has not been examined yet.

CITATION LIST

Patent Literature

Patent Document 1: JP-A-2010-286279

Non Patent Literature

Non-Patent Document 1: J Leukoc Biol. 2002 72(3): 478-85.2002

SUMMARY OF INVENTION

Technical Problem

The present inventors have tried to produce a calibration sample solution containing LRG. As a result, it was found that, when LRG is added to a solution having a pH of less than 7, the stability of LRG is poor, and LRG is gradually decomposed and lost with the time.

An object of the invention is to provide a leucine-rich α2 glycoprotein composition which contains leucine-rich α2 glycoprotein and which has high preservation stability.

Solution to Problem

As a result of further investigation, the inventors have found that the stability of LRG improves when the pH of a solution containing LRG is kept in a specific range. It was also found that the stability of LRG further improves when the solution has a salt concentration in a specific range. The invention is based on the findings.

Specifically, the invention is as follows:

<1> a leucine-rich α2 glycoprotein composition comprising leucine-rich α2 glycoprotein, wherein a pH of the composition is 7.0 to 9.3, <2> the leucine-rich α2 glycoprotein composition according to <1>, which is a calibration sample solution for measuring the leucine-rich α2 glycoprotein, <3> the leucine-rich α2 glycoprotein composition according to <1> or <2>, which is filled in a preservation container, <4> the leucine-rich α2 glycoprotein composition according to any one of <1> to <3>, wherein the pH of the composition is 7.8 to 9.0, <5> the leucine-rich α2 glycoprotein composition according to any one of <1> to <4>, wherein a concentration of a salt of the composition is 200 mM to 800 mM, <6> the leucine-rich α2 glycoprotein composition according to <5>, wherein the salt is a metal salt, <7> a method for measuring leucine-rich α2 glycoprotein comprising:

using the leucine-rich α2 glycoprotein composition according to any one of <1> to <6>, <8> a kit for measuring leucine-rich α2 glycoprotein comprising the leucine-rich α2 glycoprotein composition according to any one of claims <1> to <6>, <9> a preservation stabilizing method for leucine-rich α2 glycoprotein comprising: bringing leucine-rich α2 glycoprotein into contact with a solvent having a pH of 7.0 to 9.3, <10> the preservation stabilizing method for leucine-rich α2 glycoprotein according to <9>, wherein the pH of the solvent is 7.8 to 9.0, <11> the preservation stabilizing method for leucine-rich α2 glycoprotein according to <9> or <10>, wherein a concentration of a salt in the solvent is 200 mM to 800 mM, and <12> the preservation stabilizing method for leucine-rich α2 glycoprotein according to any one of <9> to <11>, wherein the salt is a metal salt.

Advantageous Effects of Invention

According to the invention, an LRG-containing composition which contains leucine-rich α2 glycoprotein and which has excellent preservation stability, especially an LRG-containing calibration sample can be provided. Therefore, according to the invention, LRG in a biological sample can be quantitatively measured accurately, and disease can accurately be diagnosed.

BRIEF DESCRIPTION OF DRAWINGS

FIG. 1 A graph showing the changes in LRG amount of solutions having various pH values with time, where the initial values are regarded as 100%.

FIG. 2 A graph showing the changes in LRG amount of solutions having various salt concentrations with time, where the initial values are regarded as 100%.

FIG. 3 A graph showing the changes in LRG amount of solutions having various pH values with time, where the initial values are regarded as 100%.

DESCRIPTION OF EMBODIMENTS (Leucine-Rich α2 Glycoprotein)

Leucine-rich α2 glycoprotein or LRG is a glycoprotein of about 50 kDa. LRG is one of serum proteins, and it is said that about 3.0 µg/mL is contained in the serum of a healthy individual. It is reported that LRG is secreted from neutrophils. The relevance of a change in the LRG amount in the body to various diseases, for example, to tuberculosis or a tumor, has been studied recently, and it is required to accurately measure the amount of LRG in the living body to accurately diagnose these diseases.

LRG can be measured using a known method such as an immunological method. The immunological methods include ELISA, enzyme immunoassay, surface plasmon resonance, latex agglutination immunoassay (LTIA), chemiluminescence immunoassay, electrochemiluminescence immunoassay, fluorescent antibody technique, radioimmunoassay, immunoprecipitation, Western blotting, immunochromatography, high performance liquid chromatography (HPLC) and the like.

As the LRG contained in the composition of the invention, commercially available LRG may be used, and LRG which has been produced or purified by a user may also be used. As the LRG contained in the composition of the invention, LRG which has been produced in vitro may be used, and LRG which has been extracted from a living body may also be used.

(pH)

Considering the stability of LRG, the pH of the leucine-rich α2 glycoprotein composition of the invention is 7.0 to 9.3, preferably 7.0 to 9.0, more preferably 7.5 to 9.0, further preferably 7.8 to 9.0, most preferably 8.0 to 9.0.

The pH can be adjusted using a pH adjusting reagent known to one skilled in the art such as sodium hydroxide.

(Salt Concentration)

The salt concentration of the LRG composition of the invention is preferably 200 mM to 800 mM, more preferably 300 mM to 700 mM, most preferably 300 mM to 600 mM. By keeping the salt concentration within this range, the stability of LRG can be further improved.

As the kind of the salt contained in the LRG composition of the invention, any known salt can be used, and for example, metal salts such as sodium salts, potassium salts and magnesium salts as well as nonmetal salts such as ammonium salts and amine salts can be used. A metal salt is preferably used, and a sodium salt is more preferably used. To supply a sodium salt, sodium chloride is most preferably used. More than one kind of salt can also be used in combination.

(Leucine-Rich α2 Glycoprotein Composition)

In the present specification, the leucine-rich α2 glycoprotein composition (hereinafter, sometimes referred to as the LRG composition) means a solution containing LRG which is used for measuring LRG. The LRG composition of the invention can be suitably used as a calibration sample solution for LRG measurement. In the specification, the calibration sample solution means a sample solution containing the substance to be measured at a certain concentration which is used for accurately measuring the substance to be measured, and a standard substance, a calibrator, a control, an internal standard substance and the like are the calibration sample solutions. A form for supplying the LRG composition of the invention is a form in a solution state prepared in advance by mixing LRG and a solvent having a pH of 7.0 to 9.3. Another form for supplying the LRG composition of the invention is a form in which LRG and the solvent are prepared separately and in which the two are mixed into a solution state before the use.

The concentration of LRG in the LRG composition of the invention can be 0.1 to 1000 µg/mL, 0.1 to 100 µg/mL, 1 to 100 µg/mL, 1 to 50 µg/mL or 1 to 30 µg/mL although the concentration is not limited to the ranges.

In this regard, "using the leucine-rich α2 glycoprotein composition" in the method for measuring leucine-rich α2 glycoprotein means that the leucine-rich α2 glycoprotein composition is used to accurately measure leucine-rich α2 glycoprotein and means that the leucine-rich α2 glycoprotein composition is used as a calibration sample solution (a standard substance, a calibrator, a control, an internal standard substance and the like) for example.

The composition of the LRG composition of the invention is not particularly limited except that the LRG composition contains LRG and has a pH of 7.0 to 9.3, as far as the effects of the invention are not impaired, and the uses of LRG are not obstructively affected. When LRG is measured by an immunological measurement method, the effects of the invention should not be impaired, and the whole or a part of the reaction constituting the measurement system such as antigen-antibody reaction, labeling reaction for detection with biotin/avidin and enzymatic reaction should not be interrupted. A component which is generally used in an immunological measurement method, for example, a buffer such as acetic acid, citric acid, phosphoric acid, HEPES, MES, Tris, glycine, boric acid, carbonic acid and a Good's buffer, a component for inhibiting non-specific reaction (a nonionic surfactant such as Tween20 (TM of Sigma-Aldrich containing polyethylene glycol sorbitan monolaurate, which is a nonionic surfactant) and TritonX-100 (TM of Sigma-Aldrich containing t-octylphenoxypolyethoxyethanol) or the like), a component which promotes antigen-antibody reaction (a polymer such as polyethylene glycol, polyvinylpyrrolidone and a phospholipid polymer or the like), a glycoprotein other than LRG or a peptide (albumin, casein or the like), an amino acid, a saccharide (sucrose, cyclodextrin or the like), a preservative (sodium azide, ProClin950 (TM of Sigma-Aldrich containing 2-methyl-4-isothiazolin-3-one as the active ingredient) or the like) or the like can be appropriately selected and used depending on the purpose.

The LRG composition of the invention can be preserved in a known container. The material of the preservation container that can be used for the LRG composition of the invention can be polypropylene, polystyrene or glass although the material is not limited to these materials. The form of the preservation container may be either a hard type or a soft type, and examples include an ampule, a vial, a soft bag, an injection-type container and the like.

LRG can be produced by LRG-expressing cells. The LRG-expressing cells can be obtained by transformation of a host with an expression vector containing DNA encoding LRG. The host cells can be microorganism cells, insect cells, mammalian cells or the like, which are prokaryotes or eukaryotes. As the mammalian cells, for example, HepG2 cells, HEK293 cells, HeLa cells, human FL cells, monkey COS-7 cells, monkey Vero cells, Chinese hamster ovary cells (abbreviated to CHO cells below), dhfr gene-knockout CHO cells, mouse L cells, mouse AtT-20 cells, mouse myeloma cells, rat H4IIE-C3 cells, rat GH3 cells and the like can be used.

A plasmid obtained in the above manner can be introduced into the host cells by a general genetic engineering method. The transformant can be cultured by a general method used for culturing microorganisms or culturing insect cells or mammalian cells. The LRG protein can be obtained by a combination of methods which are generally used for isolation/purification of general proteins.

In the specification, "preservation stabilizing" or that "the stability improves" means that, because most of LRG contained in a solution containing LRG is maintained without being decomposed or without a structural change for a long time, the initial LRG value of the solution and the measured value after preservation do not differ greatly. More specifically, for example, it means that, because 75% or more of LRG contained in a solution containing LRG is maintained without being decomposed or without a structural change for 29 days, the measured LRG value of the solution after preservation at 37° C. for 29 days is 75% or more of the initial value. The LRG composition of the invention has a measured LRG value after preservation at 37° C. for 29 days of, based on the initial amount, preferably 80% or more, more preferably 90% or more, further preferably 95% or more, most preferably 96% or more. The LRG composition of the invention has long-term stability also at a high temperature of 37° C., but an LRG composition which is preserved at a low temperature or at normal temperature is not excluded from the scope of the invention.

(Biological Sample for LRG Measurement)

The biological sample for the measurement of LRG is not particularly limited as long as LRG can be measured but is blood, serum, plasma, cerebral spinal fluid (CSF), urine, stool or the like. Serum or plasma is preferably used, and serum is further preferably used. The living body or the subject is not particularly limited as long as the living body or the subject is a mammal and includes a human or an animal (for example, a monkey, a dog, a cat, a mouse, a guinea pig, a rat, a hamster, a horse, a cow and a pig), and a human is preferable. The biological sample may be appropriately subjected to pretreatment when necessary.

(Measurement Kit for Leucine-Rich α2 Glycoprotein)

With the kit for measuring leucine-rich α2 glycoprotein (hereinafter, sometimes referred to as an LRG measurement kit) of the invention, LRG can be measured accurately using an LRG composition. An example of the LRG measurement kit is a kit using an immunological method. The LRG measurement kit of the invention can include a reagent for measuring the LRG concentration of a human body by an immunological method. The immunological methods include ELISA, enzyme immunoassay, surface plasmon resonance, latex agglutination immunoassay (LTIA), chemiluminescence immunoassay, electrochemiluminescence immunoassay, fluorescent antibody technique, radioimmunoassay, immunoprecipitation, Western blotting, immunochromatography, high-performance liquid chromatography (HPLC) and the like. The immunological method is preferably latex agglutination immunoassay (LTIA).

The LRG measurement kit of the invention can be used for diagnosing autoimmune diseases, tuberculosis, tumors, inflammatory diseases and inflammatory bowel diseases (ulcerative colitis and Crohn's disease).

The LRG measurement kit of the invention can also include a user guide or the like. The kit may also include any constituent element such as a buffer, a stabilizing agent, a specimen diluent, a pH adjustment agent and a reaction container.

(Preservation Stabilizing Method for LRG Composition)

The preservation stabilizing method for the LRG composition of the invention includes a step of bringing leucine-rich α2 glycoprotein into contact with a solvent having a pH of 7.0 to pH9.3. The solvent is not particularly limited as long as the pH is 7.0 to 9.3. The solvent can contain a buffer such as HEPES, MES, CHES and Tris, and the concentration of the buffer can be 1 to 1000 mM. "Bringing into contact" includes adjusting the pH of an LRG-containing solution having a pH that is not 7.0 to 9.3 to 7.0 to 9.3 in addition to adding LRG to the solvent having a pH of 7.0 to 9.3.

Next, the invention is explained specifically referring to Examples, but the Examples do not limit the scope of the invention. In the specification, % indicates weight % unless otherwise explained.

EXAMPLES

Example 1

Examination 1 of Changes in LRG Amount of Solutions Having Various pH Values with Time After producing LRG standard antigen solutions having various pH values, a preservation test was conducted, and the changes in LRG amount of the LRG standard antigen solutions with time were examined. The influence of the pH on the preservation stability of LRG was thus examined. The LRG used was produced using CHO (Chinese hamster cells). Specifically, the LRG was prepared by introducing human LRG gene to CHO-K1 cells using a plasmid, culturing the LRG gene-introduced CHO-K1 cells in a serum-free medium and recovering the human LRG recombinant protein from the culture supernatant.

LRG standard antigen solutions having the composition in Table 1 below were produced, and the pH values were controlled to 7.5 or 8.0 using a 4N sodium hydroxide solution. The LRG standard antigen solutions were stored at 37° C. for 29 days, and the changes in LRG amount with time were observed. The sample composition and the experimental results are shown in Tables 1 and 2 and FIG. 1.

TABLE 1

| Component | Concentration |
| --- | --- |
| Bovine Serum Albumin (BSA PF) | 1% |
| HEPES | 50 mM |
| Sodium Chloride | 150 mM |
| TWEEN 20 | 0.01% |
| EDTA 3Na | 5 mM |
| ProClin950 | 0.05% |
| Purified Water | Necessary Amount |
| LRG | 10.0 µg/mL |

TABLE 2

| Sample No. | PH of LRG Standard Antigen Solution | Measured Value After 29 Days (Initial Measured Value is 100%) |
| --- | --- | --- |
| 1 | 7.5 | 81% |
| 2 | 8.0 | 93% |

The measured value of the LRG standard antigen solution having a pH adjusted to 8.0 after preservation at 37° C. for 29 days was 93% of the initial LRG amount. The measured value of the LRG standard antigen solution having a pH adjusted to 7.5 was 81% of the initial LRG amount. Therefore, it was shown that the preservation stability of LRG is excellent when the pH of the LRG standard antigen solution is 8.0 rather than 7.5.

Example 2

Examination of Changes in LRG Amount of Solutions Having Various Salt Concentrations with Time The concentration of sodium chloride was changed from 150 mM to 500 mM in sample No. 2 produced in Example 1, and a preservation test was conducted. The influence of the salt concentration on the preservation stability of LRG was thus examined. The sample compositions and the experimental results are shown in Table 3 and FIG. 2.

TABLE 3

| Sample No. | Salt Concentration (mM) | Measured Value After 29 Days (Initial Measured Value is 100%) |
|---|---|---|
| 2 | 150 | 93% |
| 3 | 500 | 98% |

It was shown that the preservation stability of LRG improves with the LRG standard antigen solution having an increased salt concentration of 500 mM compared to the LRG standard antigen solution having a salt concentration of 150 mM. While the measured value of the LRG standard antigen solution having a salt concentration of 150 mM after preservation at 37° C. for 29 days was 93% of the initial LRG amount, the measured value of the LRG standard antigen solution having a salt concentration of 500 mM after preservation at 37° C. for 29 days was 98% of the initial LRG amount.

Example 3

Examination 2 of Changes in LRG Amount of Solutions Having Various pH Values with Time LRG standard antigen solutions having the same composition as that of the samples prepared in Example 1 were produced except that the buffers shown in Table 4 below were used and that the pH was adjusted to 6.0, 7.0, 7.5, 8.0, 8.5, 9.0 or 9.5. The LRG standard antigen solutions were stored at 37° C. for 29 days, and the changes in LRG amount with time were observed. The sample compositions and the experimental results are shown in Table 4 and FIG. 3.

TABLE 4

| Sample No. | Buffer | pH | Measured Value After 29 Days (Initial Measured Value is 100%) |
|---|---|---|---|
| 4 | MOPS | 6.0 | 52% |
| 5 | HEPES | 7.0 | 75% |
| 6 | HEPES | 7.5 | 83% |
| 7 | HEPES | 8.0 | 100% |
| 8 | HEPES | 8.5 | 100% |
| 9 | CHES | 9.0 | 96% |
| 10 | CHES | 9.5 | 67% |

From the above results, it was shown that the preservation stability of LRG improves when the pH of the LRG standard antigen solution is adjusted to 7.0 to 9.3.

INDUSTRIAL APPLICABILITY

The leucine-rich α2 glycoprotein composition of the invention has excellent preservation stability. Thus, when the leucine-rich α2 glycoprotein composition of the invention is used as a calibration sample, LRG in a biological sample can be quantitatively measured accurately, and disease can accurately be diagnosed.

The invention claimed is:

1. A leucine-rich α2 glycoprotein solution, comprising:
   leucine-rich α2 glycoprotein;
   a preservative;
   a glycoprotein other than LRG, or a peptide;
   a non-ionic surfactant;
   a buffer;
   a metal salt;
   and
   water,
   wherein pH of the solution is 7.8 to 9.0,
   concentration of the metal salt of the solution is 300 mM to 600 mM,
   90% or more of the leucine-rich α2 glycoprotein contained in the solution containing the leucine-rich α2 glycoprotein is maintained without being decomposed or without a structural change for 29 days at 37° C., and said solution is suitable for use as a calibration sample solution for measuring leucine-rich α2 glycoprotein.

2. The leucine-rich α2 glycoprotein solution according to claim 1, which is filled in a preservation container.

3. The leucine-rich α2 glycoprotein solution according to claim 1, wherein 95% or more of the leucine-rich α2 glycoprotein contained in the solution containing the leucine-rich α2 glycoprotein is maintained without being decomposed or without a structural change for 29 days at 37° C.

4. The leucine-rich α2 glycoprotein solution according to claim 1, wherein 96% or more of the leucine-rich α2 glycoprotein contained in the solution containing the leucine-rich α2 glycoprotein is maintained without being decomposed or without a structural change for 29 days at 37° C.

5. The leucine-rich α2 glycoprotein solution according to claim 1, wherein said metal salt is a sodium salt.

6. The leucine-rich α2 glycoprotein solution according to claim 5, wherein said sodium salt is sodium chloride.

7. A kit comprising:
   (1) the leucine-rich α2 glycoprotein solution according to claim 1, the solution containing a peptide and further containing an amino acid and a saccharide, and
   (2) a buffer, a stabilizing agent, a specimen diluent, a pH adjustment agent, and a reaction container.

8. The kit according to claim 7, said solution further comprising a polymer.

9. The kit according to claim 7, said solution further comprising a polyethylene glycol, polyvinylpyrrolidone or a phospholipid polymer.

10. The leucine-rich α2 glycoprotein solution according to claim 1, wherein the glycoprotein other than LRG or the peptide is albumin or casein.

* * * * *